(12) United States Patent
Chen et al.

(10) Patent No.: US 8,273,564 B2
(45) Date of Patent: *Sep. 25, 2012

(54) **DISINFECTANT COMPOSITION COMPRISING PHAGE OF *ACINETOBACTER BAUMANNII***

(75) Inventors: Li-Kuang Chen, Hualien (TW);
Nien-Tsung Lin, Hualien (TW)

(73) Assignee: Tzu Chi Buddhist General Hospital, Hualien (TW)

( * ) Notice: Subject to any disclaimer, the term of this patent is extended or adjusted under 35 U.S.C. 154(b) by 5 days.

This patent is subject to a terminal disclaimer.

(21) Appl. No.: 12/854,814

(22) Filed: Aug. 11, 2010

(65) Prior Publication Data
US 2011/0038840 A1    Feb. 17, 2011

(30) Foreign Application Priority Data
Aug. 12, 2009 (TW) ............................... 98127069 A
Aug. 12, 2009 (TW) ............................... 98127070 A

(51) Int. Cl.
*C12N 7/00*    (2006.01)
(52) U.S. Cl. .................................................. 435/235.1
(58) Field of Classification Search .................. None
See application file for complete search history.

(56) References Cited

U.S. PATENT DOCUMENTS

| | | |
|---|---|---|
| 5,688,501 A | 11/1997 | Merril et al. |
| 5,997,862 A | 12/1999 | Fischetti et al. |
| 6,121,036 A | 9/2000 | Ghanbari et al. |
| 6,248,324 B1 | 6/2001 | Fischetti et al. |
| 6,485,902 B2 | 11/2002 | Waddell et al. |
| 6,699,701 B1 | 3/2004 | Sulakvelidze et al. |
| 7,438,901 B2 * | 10/2008 | Loessner et al. ............. 424/93.6 |

OTHER PUBLICATIONS

Joly-Guillou et al., Journal of Hospital Infection, 1990, 16:49-58.*
Ackermann et al., Arch. Virol., 1994, 135:345-354.*
Hsueh et al., Emerging Infectious Diseases, 2002, 8(8):827-832.*
Lin et al., "Isolation and characterization of ϕAB2, a novel bacteriophage of *Acinetobacter baumannii*", Research in Microbiology, pp. 1-30 (2010).

* cited by examiner

*Primary Examiner* — Stacy B Chen
*Assistant Examiner* — Nicole Kinsey White
(74) *Attorney, Agent, or Firm* — Edwards Wildman Palmer LLP; Peter F. Corless

(57) ABSTRACT

The present invention provides a disinfectant composition including a phage of *Acinetobacter baumannii* and a carrier. The present invention also provides a method for disinfecting a medical institute or a medical research institute, including the steps of applying an effective amount of a phage of *Acinetobacter baumannii* to the medical institute or the medical research institute for reducing amount of *Acinetobacter baumannii* in the medical institute or the medical research institute.

18 Claims, 5 Drawing Sheets

Figure 2:
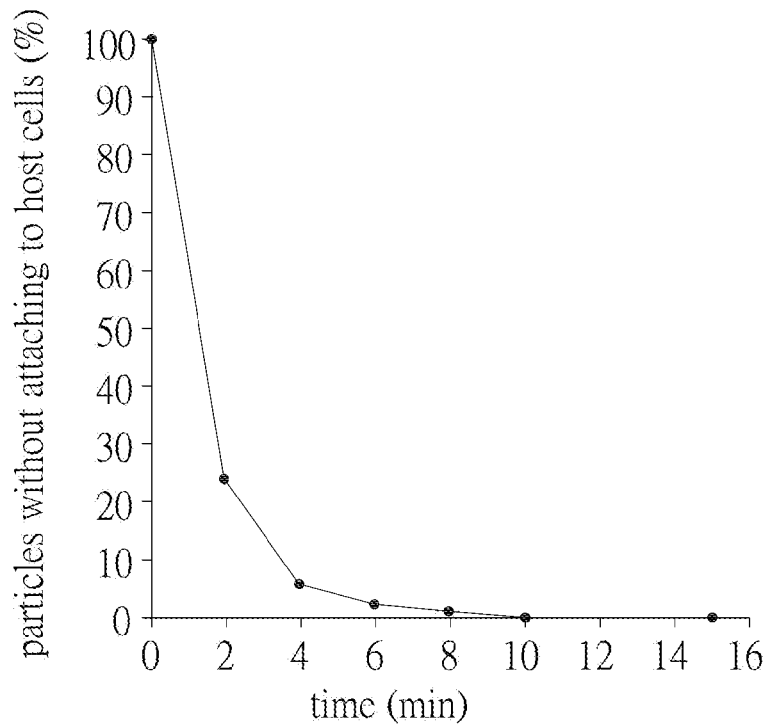

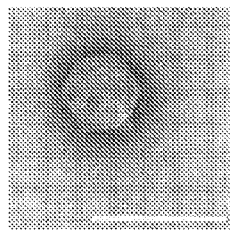 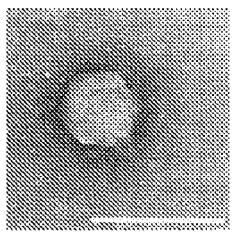 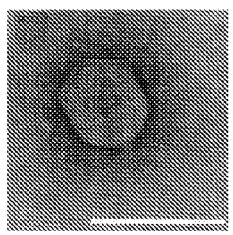 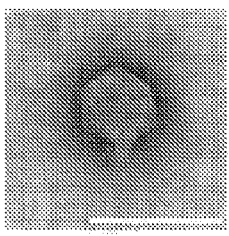
FIG. 1A    FIG. 1B    FIG. 1C    FIG. 1D
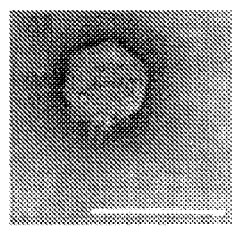 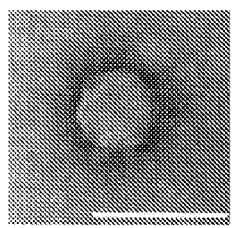 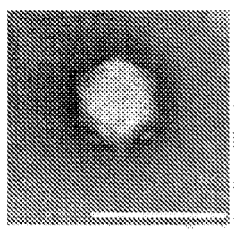 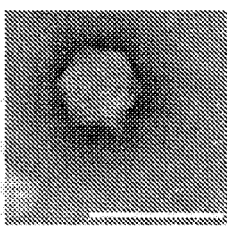
FIG. 1E    FIG. 1F    FIG. 1G    FIG. 1H
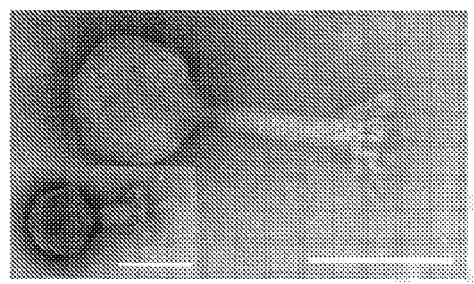 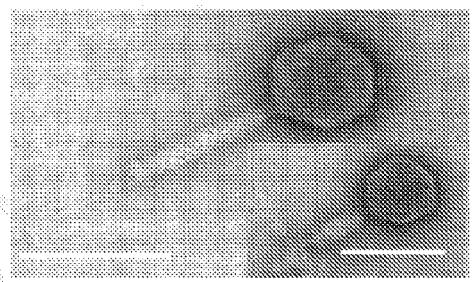
FIG. 1I          FIG. 1J

DISINFECTANT COMPOSITION COMPRISING PHAGE OF *ACINETOBACTER BAUMANNII*

CROSS-REFERENCES TO RELATED APPLICATIONS

This application claims under 35 U.S.C. §119(a) the benefit of Taiwanese Application No. 098127069 filed Aug. 12, 2009 and Taiwanese Application No. 098127070 filed Aug. 12, 2009, the entire contents of both of which are incorporated herein by reference.

1. FIELD OF INVENTION

The present invention relates to a composition and a method for disinfecting bacteria, and more particularly, to a composition comprising a phage and a carrier for disinfecting bacteria and a method using the composition for disinfecting bacteria.

2. BACKGROUND OF THE INVENTION

Nosocomial infections are tough issues. Generally, the nosocomial infection rate is about from 3% to 5%. Organisms causing nosocomial infections are usually opportunistic pathogens. In other words, these bacteria are not harmful to hosts with normal immunity, and some of them are even normal flora to human; however, while hosts have weak immunity, the bacteria cause infections, resulting in diseases.

The common bacteria causing nosocomial infections include *Staphylococcus, Pseudomonas, Acinetobacter, Enterococci, Enterobacteriaceae*, Non-fermentative gram-negative *bacilli, Legionella, Clostridium, Mycobacterium*, etc.

Currently, the most common bacteria causing nosocomial infections include *Pseudomonas aeruginosa, Staphylococcus aureus, Acinetobacter baumannii*, etc.

Bacteria causing nosocomial infections may exist in stethoscopes, anamnesis papers, tourniquets, grooves, syringe needles, respirators, humidifiers, furniture, floors, vents, monitors, water, soil, food (fruits, vegetables), dirt in drainage, human body such as skin, armpits, mucosal, oral cavity, upper respiratory tract, nasal cavity, gastrointestinal tract, etc.

For example, nosocomial infections occur in an intensive care unit since patients in the intensive care unit have weak immunity and have invasive therapies such as being cannulated. According to statistics, the nosocomial infection rate in an intensive care unit is about from 2% to 3%.

Antibiotics are general therapeutic agents for treating bacterial infections. However, when antibiotics are overused, bacteria will be selected to have resistance to the antibiotics. In current nosocomial infections, there are more and more bacteria having resistance to antibiotics, and patients infected by these bacteria have to be treated with expensive and novel antibiotics. Further, if the antibiotic resistance keeps developed, there will be no effective antibiotic for therapy. Hence, it is necessary to develop a method and/or a composition for reducing and/or preventing nosocomial infections.

Phages (bacteriophages) are viruses that infect bacteria, and grow and replicate in bacteria. There are lytic phages and lysogenic phages. Lytic phages infect bacteria, replicate in bacteria, and then are released from the bacteria by lysing and killing the bacteria. Lysogenic phages are capable of undergoing lytic or lysogenic life cycles, and exist in host cells while in lysogenic life cycles.

It has been disclosed that bacterial diseases are treated by with phages. For example, U.S. Pat. Nos. 5,688,501, 5,997,862, 6,248,324 and 6,485,902 have disclosed a pharmaceutical composition comprising phages for treating bacterial diseases, group A streptococcal infections, dermatological infections, and control of *Escherichia coli* O157 infections, respectively. U.S. Pat. No. 6,121,036 has disclosed a pharmaceutical composition having at least one phage. U.S. Pat. No. 6,699,701 has disclosed using *Salmonella enteritidis*—specific phages for packing food, in which a package material is coated with phages, and food (such as fruit and vegetables) is packed with the package material.

Accordingly, in the current applications of phages, there is no method for preventing or treating bacteria that cause nosocomial infections. Particularly, there are no phages of *Acinetobacter baumannii* and methods for reducing the amount of *Acinetobacter baumannii* (abbreviated as AB, hereafter) that cause nosocomial infections in prior art.

SUMMARY OF THE INVENTION

The present invention provides a disinfectant composition comprising a phage of *Acinetobacter baumannii* (abbreviated as AB, hereafter); and a carrier, wherein the phage specifically infects *Acinetobacter baumannii*. For example, the phage specifically infects drug-resistant AB having resistance to at least one antibiotic selected form the group consisting of gentamicin, amikacin, piperacillin/tazobactam, ticarcillin/clavulanate, ceftazidime, cefepime, cefpirome, aztreonam, imipenem, meropenem, ciprofloxacin, and levofloxacin.

In one embodiment, the phages includes at lease one pure strain of AB phage. For example, an AB phage possesses an icosahedral head and a short tail or an AB phage possesses an icosahedral head and a contractile tail. In the composition of the present invention, the phage comprised can be Podoviridae having double strained DNA genome or Myoviridae having double strained DNA genome.

In the composition of the present invention, the phage is tolerant to acid and base. In one embodiment, the phage of *Acinetobacter baumannii* has bioactivity at pH 4 to pH 12.

In one embodiment, the phage of *Acinetobacter baumannii* has bioactivity in a surfactant.

In the present invention, the term "bioactivity" refers to that the pages are capable of infecting host cells, *Acinetobacter baumannii*, replicating in the host cells and/or lysing the host cells.

In one embodiment, the phage of *Acinetobacter baumannii* is lytic phage that infects *Acinetobacter baumannii*. After the pages of the present invention infect host cells, *Acinetobacter baumannii*, the phages replicate in the host cells and released from AB host cells by lysing and killing *Acinetobacter baumannii*. Accordingly, the phages of the present invention are capable of reducing the amount of *Acinetobacter baumannii* and disinfecting environments, especially nosocomial infections caused by *Acinetobacter baumannii*.

In the composition of the present invention, the carrier is selected to be compatible with the phage of *Acinetobacter baumannii*, so as to keep the bioactivity of AB phage in the carrier.

In one embodiment, the composition can be, but not limited to, a solution, suspension, powder, spray or ointment. In the embodiment, the carrier is one selected from the group consisting of water, oil, a surfactant (such as detergent or soap), peptone and a combination thereof, and is preferably water and/or a surfactant.

In a preferred embodiment, the surfactant is at least one selected from the group consisting of an anionic surfactant, a cationic surfactant, an amphoteric surfactant and a non-ionic surfactant.

In one embodiment of the present invention, the anionic surfactant can be, but not limited to, ammonium dodecyl sulfate, disodium laureth sulfosuccinate, disodium octyl sulfosuccinate, linear dodecyl benzene sulfonates, dodecyl phosphates (mono alkyl phosphate, MAP), secondary alkane sulfates (SAS), sodium cocoyl isethionate (SCID), sodium lauryl ether sulfate (SLES), sodium lauroyl sarcosinate, sodium lauryl sulfate (SLS), sodium taurine cocoyl methyltaurate, etc.

In one embodiment of the present invention, the cationic surfactant can be, but not limited to, cetyl trimethyl ammonium chloride, dicocodimonium chloride, didoctyl dimethyl ammonium chloride, diester quaternary ammonium salts, alkyl dimethyl benzyl ammonium chloride, ditallow dimethyl ammonium chloride (DTDMAC), imidazoline quaternary ammonium salts, etc.

In one embodiment of the present invention, the amphoteric surfactant can be, but not limited to, cocoyl Imidazolinium betaine, cocoamidopropyl hydroxysultaine, cocpamidopropyl dimethyl betaine, disodium cocoamphodipropionate, lauramidopropyl betaine, sodium alkylamphopropionate, tallow dihydroxyethyl betaine, etc.

In one embodiment of the present invention, the non-ionic surfactant can be, but not limited to, alkyl polygluoside (APG), cocoamide DEA, lauramine oxide, lauryl ether carboxylic acid, Triton X (such as TX-100, TX-405, etc.), PEG-150 di-stearate, Tween (such as Tween-40, Tween-80, etc.), Span (such as Span-20, Span-80, etc.), etc.

In a preferred embodiment, the surfactant can be a commercial product, especially a detergent.

The composition of the present invention optionally comprises another phage of bacterium causing nosocomial infections.

In one embodiment, the bacterium causing nosocomial infections is at least one selected from the group consisting of *Acinetobacter, Staphylococcu, Enterococci, Enterobacteriaceae*, Non-fermentative gram-negative *bacilli, Legionella, Clostridium, Mycobacterium* and *Pseudomonas*.

In one embodiment, *Acinetobacter* includes at least one of *A. baumannii, A. calcoaceticus, A. haemolyticus, A. junii, A. johnsonii* and *A. lwoffii*.

In one embodiment, *Staphylococcu* includes at least one of *S. epidermidis, S. hemolyticus, S. auricularis, S. capitis, S. caprae, S. hominis, S. pasteuri, S. simulans, S. warneri, S. cohnii, S. sciuri, S. xylosus* and *S. saprophyticus*.

In one embodiment, *Enterococci* includes at least one of *Escherichia, Klebsiella pneumoniae, Proteus, Enterobacter, Citrobacter, Morganella, Salmonella, Serrartia, Shigella* and *Yersinia*.

In one embodiment, the bacterium causing nosocomial infections is *Pseudomonas aeruginosa*.

The composition of the present invention comprises another phage, which is a lytic phage. After the lytic page of the present invention infects host cells (bacteria), the phages replicate in the host cells and lyses cell walls of host cells, and then the host cells are destructed. Accordingly, such phage of the present invention is capable of inhibiting the bioactivity or reducing the amount of bacteria and disinfecting environments.

In one embodiment, the composition of the present invention comprises another phage, which has bioactivity in a surfactant.

Figure 5A:
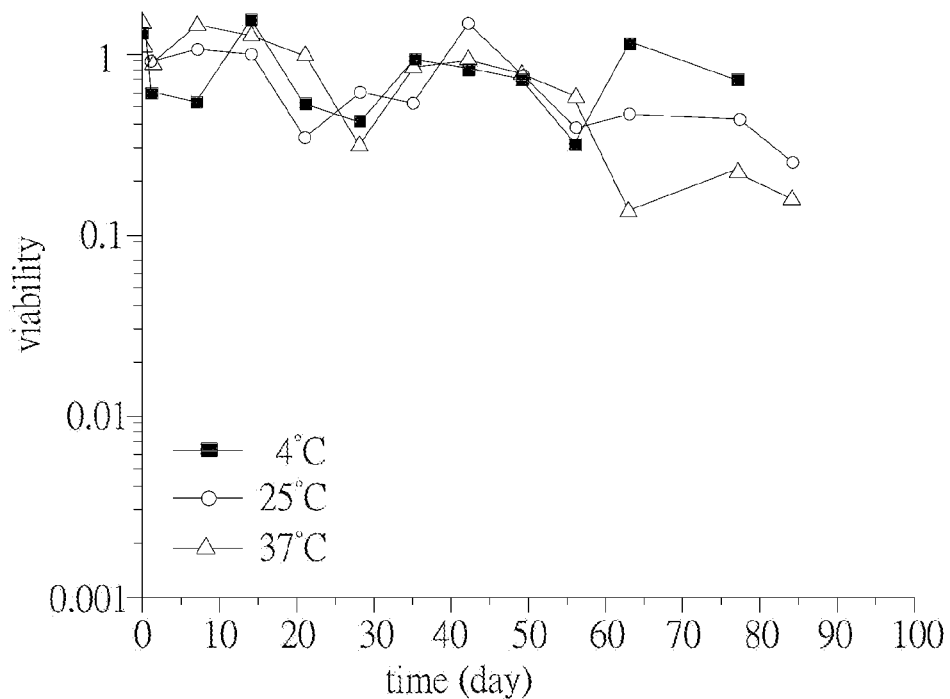
Figure 5B:
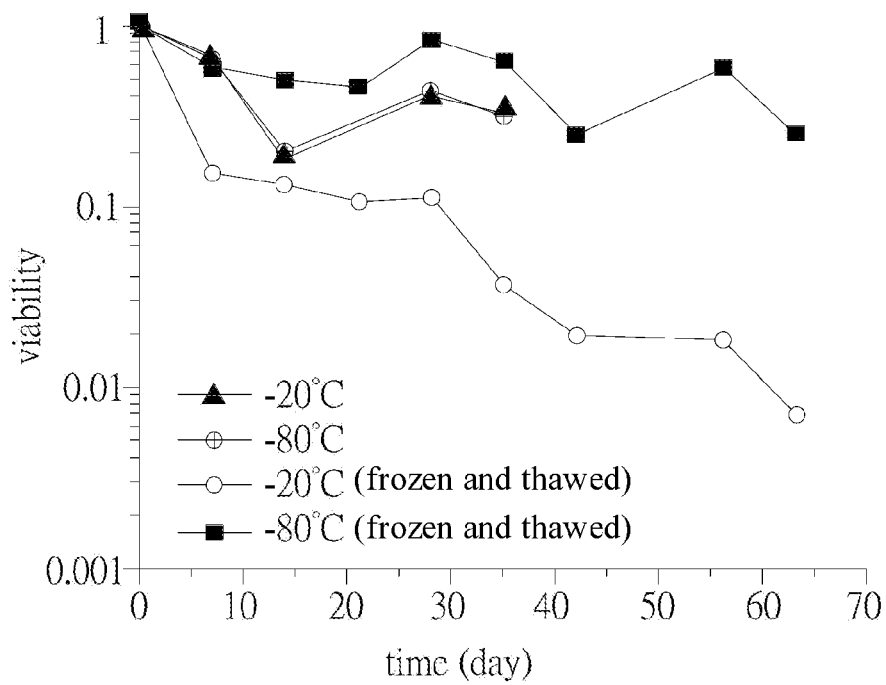
Figure 6:
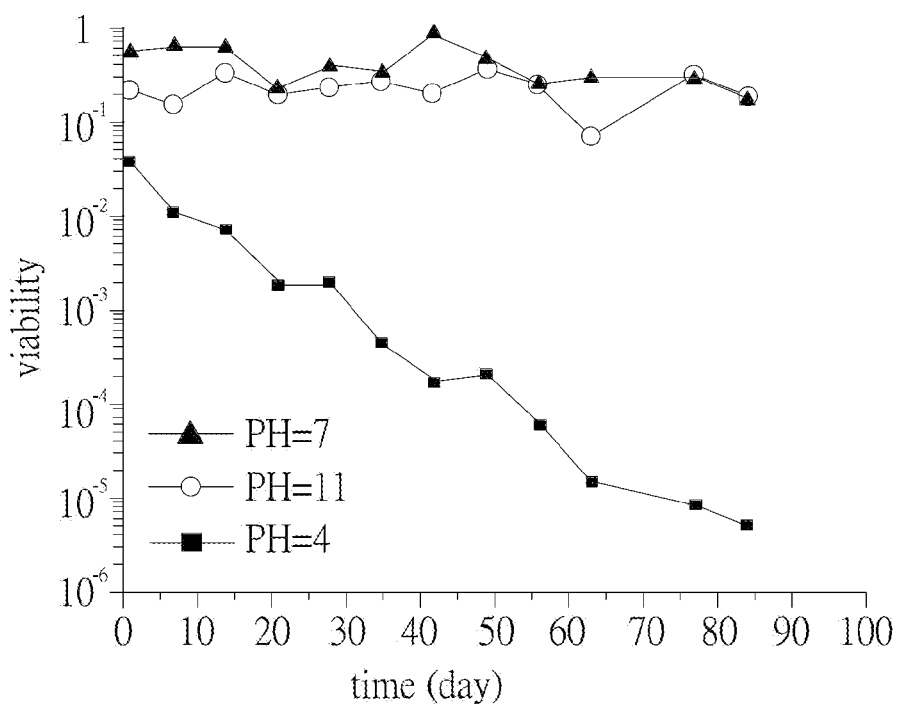
Figure 7:
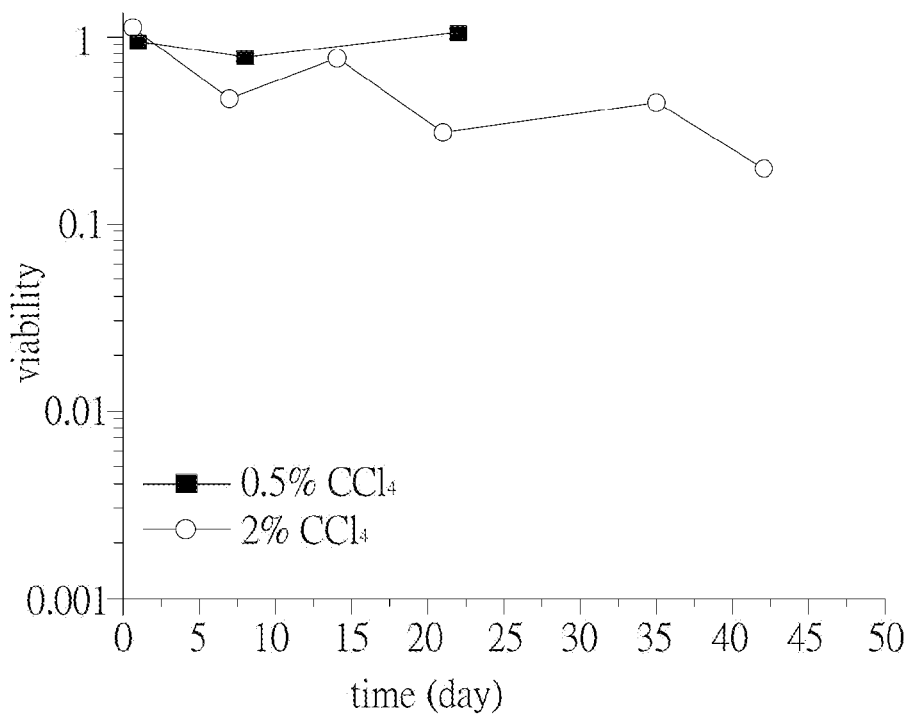

In one embodiment, an initial concentration the phage of *Acinetobacter baumannii* in the composition is $1\times10^7$ PFU/ml to $1\times10^9$ PFU/ml. The phage of *Acinetobacter baumannii* can be optionally mixed with phages to other bacteria for the composition, so as to simultaneously reduce multiple kinds of bacteria.

In another aspect, the present invention provides a method for disinfecting a medical institute or a medical research institute in vitro, comprising the step of applying the composition having a phage and a carrier in the medical institute or the medical research institute, for reducing amount of bacteria in the medical institute or the medical research institute, wherein the phage and carrier are defined as above description. In one embodiment, the method of the present invention is used for reducing amount of *Acinetobacter baumannii*, wherein the phage and carrier are defined as above description.

Optionally, the composition further comprises another phage, which is defined as above description. Therefore, the phage of *Acinetobacter baumannii* can be alone or combined with another phages for other bacteria to form the composition for reducing amount of *Acinetobacter baumannii* or simultaneously reduce multiple kinds of bacteria.

In one embodiment, the disinfectant composition is used in a medical institute, such as a hospital or a sanitarium, or a medical research institute. In one embodiment, the disinfectant composition is used in environments of a hospital or sanitarium, which can be, but not limited to, being applied to intensive care units, surgeries, recovery rooms, consulting rooms and conference rooms, or equipments in hospitals and sanitaria, which can be, but not limited to, stethoscopes, anamnesis papers, tourniquets, grooves, syringe needles, respirators, humidifiers, furniture, floors, vents and monitors. Depending on the object, which the composition is applied for, the composition can be used via directly spraying, indirectly spraying, immersing or applying to. For example, grease the composition of the present application to human skin.

In accordance with the disinfectant composition and method of the present invention, the amount of target bacteria is reduced and bioactivity of the target bacteria is inhibited due to specificities between phages and host cells. Further, the disinfectant composition of the present invention does not cause resistance of bacteria to antibiotics. The disinfectant composition of the present invention can be used with a commercial detergent. Moreover, the method of the present invention is simple, effective, having no chemical toxicity, and making no resistance of bacteria to antibiotics, such that the method of the present invention can reduce nosocomial infections.

BRIEF DESCRIPTION OF THE DRAWINGS

FIGS. 1A-1J show the electron micrographs of *Acinetobacter baumannii* phages used in the disinfectant composition according to the present invention;

FIG. 2 shows the absorption of *Acinetobacter baumannii* phage to AB according to one embodiment of the present invention;

FIG. 3 shows the one-step growth curve of *Acinetobacter baumannii* phage on host according to one embodiment of the present invention;

FIG. 4 shows the bioactivity of *Acinetobacter baumannii* phages in surfactants according to the present invention;

FIG. 5A shows the stability of the disinfectant composition at different temperatures according to the present invention;

FIG. 5B shows the stability of the disinfectant composition at different temperatures and thaw conditions according to the present invention;

FIG. 6 shows the stability of the disinfectant composition at different pH according to the present invention; and FIG. 7 shows the stability of the disinfectant composition in chemicals according to the present invention.

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

EXAMPLE 1

Preparation of phages: samples were collected from washing solution of catheter, waste water from drainage systems and untreated waste water in Buddhist Tzu Chi General Hospital, Hualien. The samples were respectively centrifuged at 5,000×g for 10 minutes, and then the supernatants were filtered via filters of 0.45 μm for plaque tests.

10 μl of filtrate was dropped to bacterial lawns of *Acinetobacter baumannii*. If there were phages in the filtrate, there would be clear zones on the bacterial lawns. Then, the clear zones were picked up and immersed in LB medium, which was filtered to remove bacteria, so as to obtain high concentrated phage solution. Subsequently, the concentrated phage solution was diluted, and plated on the LB plate to form plaques. Single plaque isolation process was performed for at least twice to obtain pure phages.

After identification, there were ten strains of *Acinetobacter baumannii* phages obtained in the present invention, named as φAB1-9 and φAB11. As shown in FIGS. 1A-1H, each of φAB1-7 and φAB9 possesses an icosahedral head and a short tail (φ AB1, deposition No.: DSM 23599; φAB2, deposition No.: DSM 23600). As shown in FIGS. 1I and 1J, both of φAB8 and φAB11 possesses an icosahedral head and a contractile tail.

EXAMPLE 2

In order to test the host cell specificity of phages obtained in the present invention, 127 strains AB were used, in which 125 strains were collected from Buddhist Tzu Chi General Hospital, Hualien, and 2 strains (ATCC 19606 and ATCC 17978) were obtained from ATCC (American Type Culture Collection).

The bacteria were cultured in the LB medium (Difco Laboratories, Detroit, Mich., USA) at 37° C., and the bacterial growth was monitored by turbidity at OD600. When OD unit was 1, the bacterial concentration was $3 \times 10^8$ cells/ml. Bacterial lawns were prepared by covering 1.8% of LB agar plate with a layer of 0.7% of LB agar having host cells (strains as listed in Table 1, and 127 AB strains mentioned above).

10 μl of phage (pure strain or mixture) solution ($10^{10}$ PFU/ml) was dropped into the bacterial lawns. The agar plate was dried for 10 minutes in the laminar flow, and then incubated at 37° C. for 18-20 hours. Subsequently, the production of plaques was observed.

TABLE 1

| Species Strains | Features | Source |
|---|---|---|
| *Acinetobacter calcoaceticus* | | |
| 33305 | ATCC Standard strains | ATCC |
| *Escherichia coli* | | |
| DH5α | endA1 hsdR17 (rk– mk+) supE44 thi-1 recA1 gyrA relA1φ80d lacZΔM15Δ(lacZYA-argF)U169 | Hanahan D. (1983) |
| G0003, G0004, G0008, G0010, G0012, G0070, G0071, G0072, G0081 | Clinical Strain | Buddhist Tzu Chi General Hospital, Hualien |
| *Klebsiella pneumoniae* | | |
| Kp2, Kp50, Kp53, Kp90, Kp120, Kp121 | Clinical Strain | Wu et al. (2007) |
| *Pseudomonas aeruginosa* | | |
| Pa79, Pa81, Pa86 | Clinical Strain | Wu et al. (2007) |

As a result, the AB phages (mixture or pure strain) obtained from example 1 formed no plaque on the bacterial lawns of *A. calcoaceticus*, 10 strains of *E. coli*, 6 strains of *K. pneumoniae* and 3 strains of *P. aeruginosa* (listed in Table 1), and plaques were only formed on the bacterial lawns of *Acinetobacter baumannii*. Hence, the phages of the present invention specifically infected *Acinetobacter baumannii*. In particular, among the 127 AB strain tested, phages φAB 1, φAB2, φAB3, φAB4, φAB5, φAB6, φAB7, φAB 8, φAB9 and φAB11 specifically infected 25, 25, 4, 20, 28, 4, 29, 9, 21 and 29 isolates of AB, respectively. In addition, phages φAB1, φAB2, φAB3, φAB4, φAB5, φAB6, φAB7, φAB8, φAB9 and φAB11 collectively lysted 89% (113/127) of the AB isolates, wherein 110 susceptible isolates were multidrug-resistant strains of AB (MDRAB). Since these phages were all capable of infecting *Acinetobacter baumannii* strains with different infectivity, the disinfectant composition according to the present application could comprises at least one AB phages.

The result indicates that all the phages obtained from example 1 were capable of forming clear zone on AB lawn, and infecting clinically separated *Acinetobacter baumannii* having multiple resistances, wherein, φAB2 (possesses an icosahedral head of 60 nm and a short tail of 9-11 nm for attaching to host cell) were capable of infecting the two standard strains obtained from ATCC, in addition to clinically separated *Acinetobacter baumannii* having multiple resistances. Hence, the phages of the present invention and the composition containing the same can reduce nosocomial infections and *Acinetobacter baumannii* having multiple resistances.

EXAMPLE 3

The AB culture (host cell) was incubated to $OD_{600}$ as 0.6 U, and then the *Acinetobacter baumannii* phages (pure strain or mixture) were added to the host cell culture (MOI: 0.0005) and incubated at room temperature. At the time points of 0, 1, 2, 3, 4, 5, 10, 20 and 30 min, 100 μl of culture was sampled and diluted with 0.9 ml of cold LB, and then centrifuged at 12,000×g for 5 minutes. The supernatant was collected, and the amount of the phage without attaching to host cells was determined. The result is shown in FIG. 2.

Upon observation of the host cell culture added with the phages, the culture solution turned from turbid into clear in 100 minutes. It is proved that the host cells were all lysed, and thus the disinfectant composition of the present invention has disinfection effects.

As shown in FIG. 2, about 75% of the phage particles attached to the host cells in 2 minutes, about 95% of the phage particles attached to the host cells in 4 minutes, and all the phage particles attached to the host cells in 10 minutes.

Figure 3:
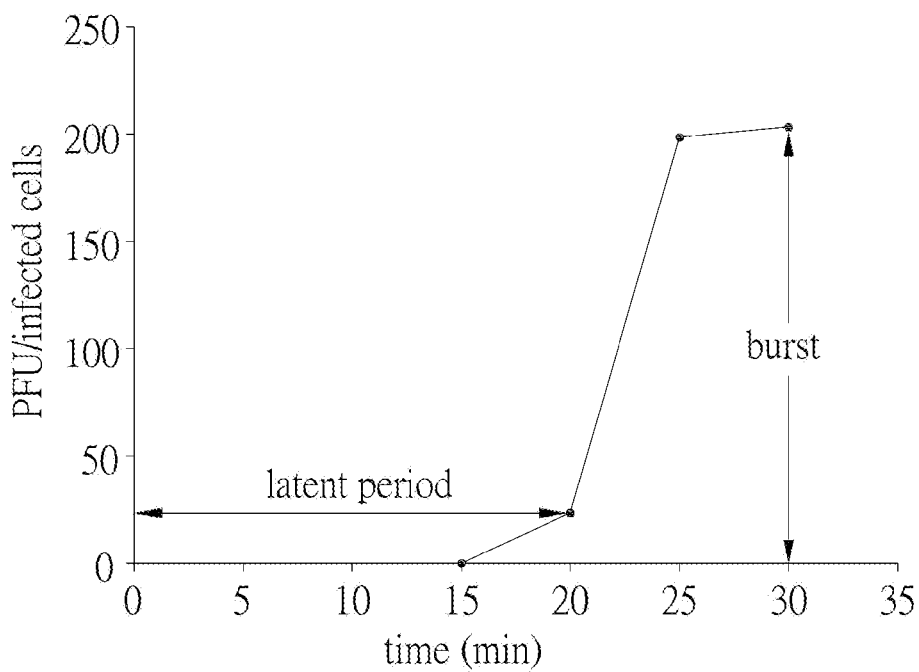

Further, the replication curve of the phages was determined by one-step growth curve. The AB culture solution ($OD_{600}$: 0.8U) was centrifuged, and the precipitant was collected and resuspended in 0.8 ml of LB medium to make concentration as $10^9$ CFU/ml. The AB phages (MOI: 0.0001) were added to the host cell culture solution, and placed at 4° C. for 30 minutes, such that the phages attached to the host cells. The mixture was centrifuged at 12,000×g for 10 minutes, and the precipitant including the infected bacteria was re-suspended with 20 ml of LB medium, and incubated at 37° C. The culture was sampled every 5 minutes, and the samples were immediately diluted and quantified. The result is shown in FIG. 3.

The definition of a latent period is from the attachment (excluding 10 minutes of the pretreatment) to the beginning of the first burst (bacteria were lysed, and phages were released). As shown in FIG. 3, the latent period is 15 minutes. The ratio of the amount of phage particles to the initial amount of the infected bacteria was calculated. The average burst is about 200 PFU/cell.

Accordingly, the results showed that the phages comprised in the disinfectant composition of the preset invention had strong infectivity, short latent period, big burst and immediate disinfection effects, and a lot of phages were released in the environment after lysing host cells so as to extend the disinfection effects.

EXAMPLE 4

The AB-specific phages isolated in example 1 were mixed with the surfactants TWEEN 20, TWEEN 80 and Triton X-100 (Sigma-Aldrich Biotechnology, USA) for preparing a disinfectant composition of the present invention.

Figure 4:
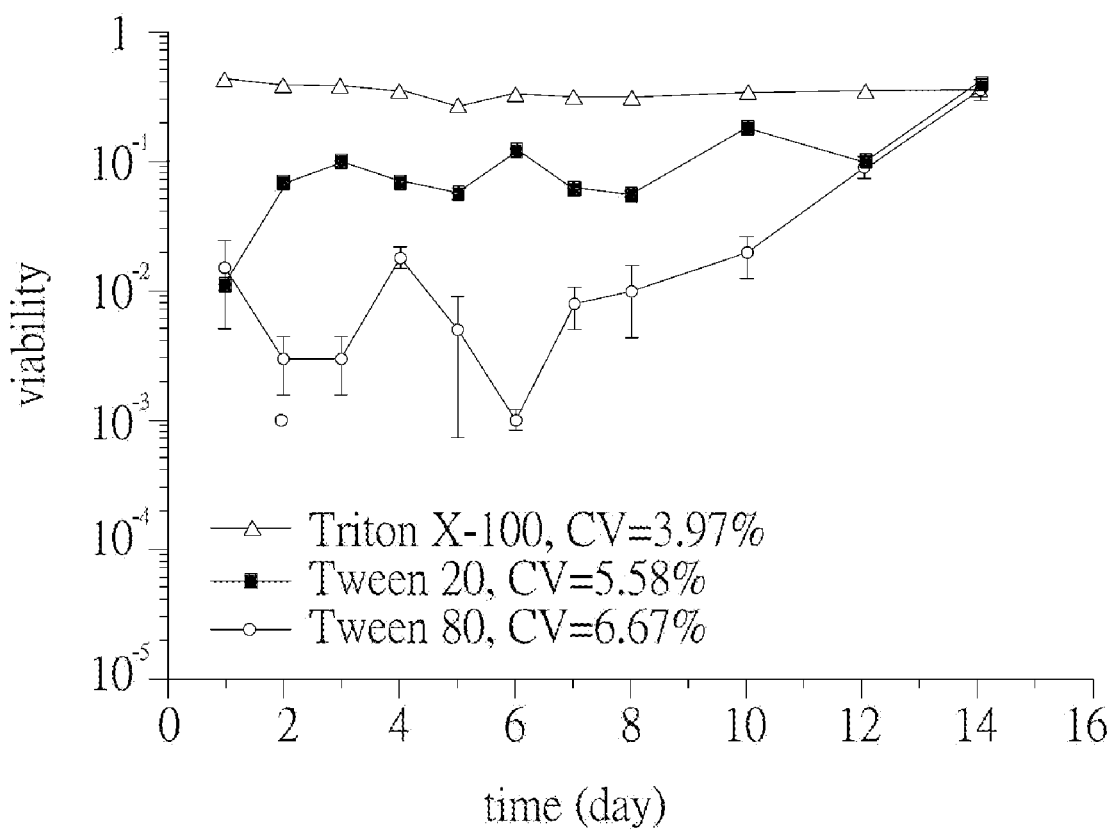

The common concentration of the conventional surfactants is 0.1~1 wt %. Thus, 0.1~1 wt % of the above surfactants was mixed with the AB phages (initial concentration: $5 \times 10^7$ PFU/ml). The mixture was incubated at room temperature, and the concentration of phage culture was determined every 24 hours. The viability of phages was calculated based on the following equation, so as to determine the effects of surfactants on the phages.

viability of phages=concentration of sampled phage culture/original concentration of phage culture FIG. 4 shows the results while using 1 wt % of surfactants.

Upon determination, the activity of phages was not influenced by 0.1~1 wt % of surfactants. As shown in FIG. 4, the phages had excellent stability in Triton X-100 and TWEEN 20, and moreover, the phages had varied viability in TWEEN 80 but still had infectivity to host cells. As shown in FIG. 4, the concentration of phages was decreased slightly and then increased gradually. It was known that by using coefficient variation, CV values of the three surfactants were all less than 20%. Accordingly, the phages were very stable in these three surfactants. Accordingly, stable disinfectant composition of the present invention could be made therefrom.

Embodiment 5

The stability of the disinfectant composition of the present invention was determined under different conditions.

1. Temperature

The phages were diluted with autoclaved water to $10^8$ PFU/ml, and then placed at different temperatures, 4°, 25°, 37°, 42°, −20° and −80°. For the tests at 4°, 25° and 37°, the concentration of the phage culture was determined every 3 hours in 24 hours, and then determined every week for 12 weeks. As shown in FIG. 5A, there were respective two groups at −20° and −80°, in which one group was repeatedly frozen and thawed and the determination was performed for 12 weeks, and the other group was thawed once and the determination was performed for 5 weeks. The results were shown in FIG. 5B.

2. pH

The phages were diluted with acidic solution (pH 4) or basic solution (pH 11) to $10^8$ PFU/ml. The concentration of the phage cultures at pH 4.7, 7 and 11 was determined every 3 hours in 24 hours, and then determined every week for 12 weeks. FIG. 6 shows the results.

3. Chemicals

The phages were added to chloroform solution (0.5% and 2%, respectively), and the phages were diluted to $10^8$ PFU/ml. The concentration of the phage culture was determined every 3 hours in 24 hours. Then, the concentration of the phage culture in 0.5% chloroform solution was determined every week for 3 weeks, and the concentration of the phage culture in 2% chloroform solution was determined every week for 6 weeks. FIG. 6 shows the results.

4. Dry Treatment $10^{10}$ PFU/ml of phages were grouped into groups A and B. Groups A and B of the phages were diluted with peptone ad autoclaved water, respectively, for ten folds, and then dried in the speed vac system. After dry treatment, groups A and B of the phages were respectively dissolved in 0.5 ml of peptone and 0.5 ml of autoclaved water. The concentrations of the phages before and after the dry treatment were determined and shown in Table 2.

TABLE 2

| | Average concentration of phages after dry treatment (PFU/ml) | Original concentration of phages (PFU/ml) | Viability of re-dissolved phages |
|---|---|---|---|
| Group A | $2.18 \times 10^9$ | $1.02 \times 10^{10}$ | 21.3% |
| Group B | $2.30 \times 10^9$ | $1.02 \times 10^{10}$ | 33.4% |

According to the above results, the phages in the disinfectant composition of the present invention survived for at least 8 weeks at low temperatures (−20°, −80°, 4°), and had the viability more than 5%. At 25° C. and 37° C., the phages survived for at least 11 weeks and had the viability more than 14.9%. At 42° C. for 2 weeks, the phages had the viability as 14.8%.

The phages in the disinfectant composition of the present invention incubated at pH 11 for about 11 weeks had the viability as about 30%. It was observed that the phages incubated at pH 4 survived for 11 weeks. In addition, the phages in the disinfectant composition of the present invention in 0.5% and 2% chloroform solution survived for at least 3 weeks and had the viability as 30%. After dry treatment and re-dissolution, the viability of phages was more than 20%.

Accordingly, the phages of the present invention have tolerance to temperatures, humidity, pH and chemicals, and maintain good viability. It appears that the disinfectant composition of the present invention is very stable.

EXAMPLE 6

Test of disinfection effects: bacteria ($10^7$ CFU/ml) with the same concentration were respectively placed in the containers with the same specification, and the disinfectant composition having $10^7$ PFU/ml of phages was sprayed in the container. Sampling was performed at different time points, and then concentrations of bacteria and phages were determined according to the standard procedure. The disinfection effect was indicated by the reduction amount of bacteria.

The disinfectant composition of the present invention includes the following ingredients:

(1) phage of *Acinetobacter baumannii* and autoclaved water (2) phage of *Acinetobacter baumannii* and surfactants (3) phage of *Acinetobacter baumannii*, autoclaved water and surfactants (4) phage of *Acinetobacter baumannii*, another phage (phage of *Staphylococcus*) and autoclaved water (5) phage of *Acinetobacter baumannii*, another phage (phage of *Staphylococcus*) and surfactants (6) phage of *Acinetobacter baumannii*, another phage (phage of *Staphylococcus*), autoclaved water and surfactants In addition, the control test was that autoclaved water was sprayed in the container.

It was observed that in the containers having the disinfectant compositions of the present invention, the mixture turned from turbid into clear, which indicated that the host cells, bacteria, were completely lysed by the phages, and the bacterial amount was effectively reduced for several logs. It was proved that the disinfectant composition of the present invention had disinfection effects.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A disinfectant composition, comprising:
a lytic phage of *Acinetobacter baumannii*; and
a carrier,
wherein the phage is compatible with the carrier so as to keep bioactivity of the phage; and
wherein the phage of *Acinetobacter baumannii* possesses an icosahedral head and a short tail.

2. The disinfectant composition of claim 1, wherein the phage of *Acinetobacter baumannii* comprises at least one pure strain of *Acinetobacter baumannii* phages.

3. The disinfectant composition of claim 1, wherein the phage of *Acinetobacter baumannii* specifically infects *Acinetobacter baumannii*.

4. The disinfectant composition of claim 1, wherein the *Acinetobacter baumannii* is drug-resistant *Acinetobacter baumannii*.

5. The disinfectant composition of claim 4, wherein the drug-resistant *Acinetobacter baumannii* has resistance to at least one antibiotics selected form the group consisting of gentamicin, amikacin, piperacillin/tazobactam, ticarcillin/clavulanate, ceftazidime, cefepime, cefpirome, aztreonam, imipenem, meropenem, ciprofloxacin, and levofloxacin.

6. The disinfectant composition of claim 1, wherein the phage of *Acinetobacter baumannii* is a Podoviridae phage having a double stranded DNA genome.

7. The disinfectant composition of claim 1, further comprising a phage of *Acinetobacter baumannii* possessing an icosahedral head and a contractile tail.

8. The disinfectant composition of claim 7, wherein the phage of *Acinetobacter baumannii* possessing an icosahedral head and a contractile tail is a Myoviridae phage having a double stranded DNA genome.

9. The disinfectant composition of claim 1, wherein the phage of *Acinetobacter baumannii* has bioactivity at pH 4 to pH 12.

10. The disinfectant composition of claim 1, being a solution, suspension, powder, spray or ointment.

11. The disinfectant composition of claim 1, wherein the carrier is one selected from the group consisting of water, oil, a surfactant, peptone and a combination thereof.

12. The disinfectant composition of claim 11, wherein the surfactant is at least one selected from the group consisting of an anionic surfactant, a cationic surfactant, an amphoteric surfactant and a non-ionic surfactant.

13. The disinfectant composition of claim 11, wherein the surfactant is a non-ionic surfactant.

14. The disinfectant composition of claim 1, further comprising another phage of bacterium causing nosocomial infections.

15. The disinfectant composition of claim 14, wherein the bacterium causing nosocomial infections is at least one selected from the group consisting of *Acinetobacter, Staphylococcu, Enterococci, Enterobacteriaceae*, Non-fermentative gram-negative *bacilli, Legionella, Clostridium, Mycobacterium* and *Pseudomonas*.

16. The disinfectant composition of claim 1, wherein an initial concentration of the phage of *Acinetobacter baumannii* is $1\times10^7$ PFU/ml to $1\times10^9$ PFU/ml.

17. A method for disinfecting a medical institute or a medical research institute, comprising the step of applying the composition of claim 1 in the medical institute or the medical research institute for reducing amount of bacteria in the medical institute or the medical research institute.

18. The method of claim 17, wherein the step of applying is performed via directly spraying, indirectly spraying, immersing or greasing.

* * * * *